(12) United States Patent
Krüger (10) Patent No.: US 10,004,540 B2
(45) Date of Patent: Jun. 26, 2018

(54) PEDICLE SCREW WITH RADIALLY OFFSET GUIDEWAY

(71) Applicant: Aesculap AG, Tuttlingen (DE)

(72) Inventor: Sven Krüger, Trossingen (DE)

(73) Assignee: Aesculap AG, Tuttlingen (DE)

( * ) Notice: Subject to any disclaimer, the term of this patent is extended or adjusted under 35 U.S.C. 154(b) by 0 days. days.

(21) Appl. No.: 15/182,937

(22) Filed: Jun. 15, 2016

(65) Prior Publication Data

US 2016/0361094 A1 Dec. 15, 2016

(30) Foreign Application Priority Data

Jun. 15, 2015 (DE) ........................ 10 2015 109 481

(51) Int. Cl.
*A61B 17/70* (2006.01)
*A61B 17/86* (2006.01)

(52) U.S. Cl.
CPC ...... *A61B 17/7032* (2013.01); *A61B 17/7074* (2013.01); *A61B 17/862* (2013.01); *A61B 17/7035* (2013.01)

(58) Field of Classification Search
CPC ..................................... A61B 17/7032–17/704
See application file for complete search history.

(56) References Cited

U.S. PATENT DOCUMENTS

| | | | |
|---|---|---|---|
| 8,308,773 B2 * | 11/2012 | Jang ................... | A61B 17/7032 606/265 |
| 8,343,191 B2 * | 1/2013 | Matthis .............. | A61B 17/7032 606/264 |
| 8,986,349 B1 * | 3/2015 | German ............. | A61B 17/7068 606/279 |
| 9,144,437 B2 * | 9/2015 | Matthis .............. | A61B 17/7031 |
| 2003/0100896 A1 * | 5/2003 | Biedermann ...... | A61B 17/7032 606/305 |
| 2004/0039383 A1 * | 2/2004 | Jackson ............. | A61B 17/7091 606/270 |
| 2004/0049196 A1 * | 3/2004 | Jackson ............. | A61B 17/7032 606/916 |
| 2004/0162560 A1 * | 8/2004 | Raynor .............. | A61B 17/7032 606/278 |
| 2004/0186473 A1 * | 9/2004 | Cournoyer ......... | A61B 17/7032 606/266 |

(Continued)

FOREIGN PATENT DOCUMENTS

| | | |
|---|---|---|
| DE | 202011100080 | 9/2011 |
| WO | 2012103660 | 8/2012 |

OTHER PUBLICATIONS

German Search Report for German Application No. 102015109481.9, dated Dec. 22, 2015 with translation, 13 pages.

*Primary Examiner* — Eduardo C Robert
*Assistant Examiner* — Michelle C Eckman
(74) *Attorney, Agent, or Firm* — RatnerPrestia (57) ABSTRACT

A bone screw includes a screw head and a seating sleeve or tulip on the screw head. The bone screw includes two sleeve flanks having a thread. A seat for a rod for surgical connection of adjacent bone screws is formed between the sleeve flanks. On at least one of the sleeve flanks, a guide surface extending in the circumferential direction for a clamping screw to be screwed into the thread is configured on the run-in side, with the guide surface offset in the radial direction vis-à-vis the thread diameter of the female thread.

18 Claims, 4 Drawing Sheets

(56) References Cited

U.S. PATENT DOCUMENTS

| | | | |
|---|---|---|---|
| 2005/0182410 A1* | 8/2005 | Jackson | A61B 17/7032 606/278 |
| 2005/0203516 A1* | 9/2005 | Biedermann | A61B 17/701 606/267 |
| 2005/0216000 A1* | 9/2005 | Colleran | A61B 17/7037 606/60 |
| 2005/0273101 A1* | 12/2005 | Schumacher | A61B 17/7037 606/306 |
| 2005/0277919 A1* | 12/2005 | Slivka | A61B 17/7032 606/256 |
| 2005/0277928 A1* | 12/2005 | Boschert | A61B 17/7037 606/328 |
| 2006/0009773 A1* | 1/2006 | Jackson | A61B 17/7032 606/266 |
| 2006/0058794 A1* | 3/2006 | Jackson | A61B 17/7032 606/272 |
| 2006/0064089 A1* | 3/2006 | Jackson | A61B 17/7037 606/308 |
| 2006/0200131 A1* | 9/2006 | Chao | A61B 17/7037 606/278 |
| 2006/0293664 A1* | 12/2006 | Schumacher | A61B 17/7037 606/254 |
| 2006/0293666 A1* | 12/2006 | Matthis | A61B 17/7032 606/86 A |
| 2007/0049933 A1* | 3/2007 | Ahn | A61B 17/7037 606/279 |
| 2007/0055240 A1* | 3/2007 | Matthis | A61B 17/7037 606/308 |
| 2007/0055241 A1* | 3/2007 | Matthis | A61B 17/7037 606/267 |
| 2007/0233122 A1* | 10/2007 | Denis | A61B 17/7032 606/247 |
| 2008/0045953 A1* | 2/2008 | Garamszegi | A61B 17/7032 606/86 A |
| 2008/0234757 A1* | 9/2008 | Jacofsky | A61B 17/7032 606/308 |
| 2008/0262556 A1* | 10/2008 | Jacofsky | A61B 17/7037 606/308 |
| 2009/0216280 A1* | 8/2009 | Hutchinson | A61B 17/88 606/279 |
| 2009/0318970 A1* | 12/2009 | Butler | A61B 17/7032 606/264 |
| 2010/0174319 A1* | 7/2010 | Jackson | A61B 17/7008 606/264 |
| 2011/0040335 A1* | 2/2011 | Stihl | A61B 17/7032 606/302 |
| 2011/0040336 A1* | 2/2011 | Hammill, Sr. | A61B 17/7037 606/305 |
| 2011/0106179 A1* | 5/2011 | Prevost | A61B 17/7037 606/308 |
| 2011/0152947 A1* | 6/2011 | Kirschman | A61B 17/7032 606/302 |
| 2011/0263945 A1* | 10/2011 | Peterson | A61B 17/0218 600/213 |
| 2012/0123480 A1* | 5/2012 | Freudiger | A61B 17/701 606/278 |
| 2012/0245640 A1* | 9/2012 | Auerbach | A61B 17/7035 606/264 |
| 2013/0046345 A1* | 2/2013 | Jones | A61B 17/7037 606/266 |
| 2013/0079830 A1* | 3/2013 | Garamszegi | A61B 17/7011 606/305 |
| 2013/0131730 A1* | 5/2013 | Jackson | A61B 17/7037 606/278 |
| 2013/0172937 A1* | 7/2013 | Davenport | A61B 17/7032 606/278 |
| 2013/0197585 A1* | 8/2013 | Jackson | A61B 17/7035 606/278 |
| 2013/0218213 A1* | 8/2013 | Lemoine | A61B 17/7032 606/305 |
| 2013/0245705 A1* | 9/2013 | McBride | A61B 17/7032 606/86 R |
| 2014/0018867 A1 | 1/2014 | Freudiger | |
| 2014/0052180 A1* | 2/2014 | Justis | A61B 17/7082 606/246 |
| 2014/0081334 A1* | 3/2014 | Jackson | A61B 17/7035 606/278 |
| 2014/0121703 A1* | 5/2014 | Jackson | A61B 17/702 606/246 |
| 2014/0142633 A1* | 5/2014 | Jackson | A61B 17/7032 606/273 |
| 2014/0277161 A1* | 9/2014 | Spratt | A61B 17/7035 606/278 |
| 2014/0343617 A1* | 11/2014 | Hannen | A61B 17/8605 606/306 |
| 2014/0350605 A1 | 11/2014 | Kirschman | |
| 2015/0032162 A1* | 1/2015 | Biedermann | A61B 17/7032 606/278 |
| 2015/0039035 A1* | 2/2015 | Kruger | A61B 17/7037 606/264 |
| 2015/0164558 A1* | 6/2015 | Jackson | A61B 17/7032 606/270 |
| 2015/0190176 A1* | 7/2015 | Jackson | A61B 17/7037 606/266 |
| 2015/0196339 A1* | 7/2015 | Trieu | A61B 17/8625 606/309 |
| 2016/0135848 A1* | 5/2016 | Chandanson | A61B 17/7037 606/266 |
| 2016/0143668 A1* | 5/2016 | Beger | A61B 17/7032 606/266 |
| 2016/0166288 A1* | 6/2016 | Biedermann | A61B 17/7037 606/266 |
| 2016/0262803 A1* | 9/2016 | Nelson | A61B 17/7032 |
| 2016/0331413 A1* | 11/2016 | Daniels | A61B 17/7032 |
| 2016/0361093 A1* | 12/2016 | Biedermann | A61B 17/7037 |
| 2017/0049482 A1* | 2/2017 | Campbell | A61B 17/7032 |
| 2017/0086886 A1* | 3/2017 | Duncan | A61B 17/7035 |
| 2017/0112540 A1* | 4/2017 | Montello | A61B 17/7025 |
| 2017/0112542 A1* | 4/2017 | Biedermann | A61B 17/7032 |
| 2017/0112543 A1* | 4/2017 | Jackson | A61B 17/7037 |
| 2017/0119438 A1* | 5/2017 | Jackson | A61B 17/862 |
| 2017/0128102 A1* | 5/2017 | Biedermann | A61B 17/7032 |
| 2017/0128103 A1* | 5/2017 | Kruger | A61B 17/7032 |
| 2017/0135729 A1* | 5/2017 | Garamszegi | A61B 17/7037 |

* cited by examiner

PEDICLE SCREW WITH RADIALLY OFFSET GUIDEWAY

RELATED APPLICATION

This application is related to and claims the benefit of priority of German Application No. DE 10 2015 109 481.9, filed Jun. 15, 2015, the content of which is incorporated by reference herein in its entirety and for all purposes.

FIELD

The present invention relates to a bone screw, especially a pedicle screw, comprising a seating sleeve or tulip provided on the screw head which has two sleeve flanks provided with a thread between which an especially slit-shaped seat for a rod for surgical connection of adjacent bone screws is formed.

BACKGROUND

Bone and pedicle screws are known from the state of the art. They serve, for example, for dorsal stabilization of the spine by means of transpedicular screwing. Pedicle screws are placed in the pedicles of respective adjacent vertebrae, whereupon an angularly stable connection is made between the respective axially superimposed pedicle screws and an axially extending rod or land. The pedicle screws and rods constitute a vertebrae stabilizing system.

A pedicle screw usually includes a screw shank extending in the axial direction and having a male thread to which a seating sleeve, the so called tulip, is connected on the screw head side. Said tulip is formed substantially U-shaped having opposite wall portions (sleeve flanks) and a gap formed therebetween and extending in the radial direction for the rod or land. The tulip is provided with a thread extending in the axial direction. The rod is inserted in the gap of the tulip and is fixed by means of a clamping screw also being referred to as set screw and being screwed with the thread.

When attaching a set screw to a pedicle screw for fixing the rod, deformation of the tulip may occur due to forces acting on the pedicle screw and especially on the tulip thereof, for example in the case of manipulation of vertebral bodies or in the case of pressing on the rod. Such deformations prevent or impede screwing of the set screw. Basically such deformations can be minimized or even prevented by an appropriate design, especially dimensioning, of the pedicle screw. However, those endeavors counteract a weight and size minimization as well as a reduction of material used. Basically two types of deformations may occur, namely those in which the thread of the tulip is deformed in the direction of the thread of the set screw and those of the opposite direction.

In the case of the first-mentioned deformations, those deformations preventing the set screw from being attached to the tulip thread are especially difficult, because the threads are no longer capable of engaging in each other. However, even in the case of minor deformation that still allows screwing the set screw may tilt relative to the axis of the tulip due to the deformation of the tulip. This may result in the fact that the thread chamfer, especially the one of the set screw, is damaged. A so called "cross threading" may occur, which means that the set screw is tilted with respect to the longitudinal axis of the screw shank and the male thread thereof so far that the start of the thread of the set screw, i.e. the run-in thread pitch or pitches, engage(s) in the wrong thread pitch of the female thread of the tulip, which may result in damage of the thread up to the uselessness of the set screw and/or the pedicle screw.

In order to reduce the impact of deformations that may disengage the threads of the tulip and the set screw, the use of appropriate thread tolerances as well as thread designs such as e.g. rectangular threads or counterdraft threads is known. Deformations of the tulip can also be reduced by the use of additional or appropriately designed instruments when screwing the set screw. For example, those instruments include a counterdraft which is engaged in the tulip and prevents or compensates and resets the deformation thereof in the radial direction. As especially for percutaneous application those instruments are intended to include, on the one hand, an as long slit as possible and, on the other hand, to have an as small outer diameter as possible, the mentioned stabilizing effect can be insufficient in a disadvantageous manner. Another drawback of such instruments is a visual impairment of the operating area. Also instruments may be used in which no counterdraft interacting with the tulip is possible or present.

From US 2014 0350605 A1 a pedicle screw system is known in which the set screw includes a chamfered head area which facilitates attaching in a female thread formed in the tulip. In addition, the female thread of the tulip includes a shortened first thread pitch so that the set screw can be inserted into the tulip and centered by means of the chamfered head area initially without any thread engagement and subsequently is rotated in said position with a thread engagement being brought about. Under certain circumstances the shortening of the thread pitch may constitute weakening of the thread in a detrimental manner.

SUMMARY

Since deformations of the pedicle screw and especially of the tulip cannot always be safely avoided, starting from the afore-described state of the art the object underlying the invention is to provide a bone screw system, especially a pedicle screw, which is robust and tolerant with respect to such deformations and facilitates and renders attaching a set screw to a bone or pedicle screw safer without additional elements or instruments such as guiding sleeves etc. being necessary or the view of the surgeon being restricted.

This object is achieved, according to the present invention, by a bone screw or pedicle screw, wherein a guide surface extending in the circumferential direction for a clamping screw adapted to be screwed into the thread is formed at (only) one of the sleeve flanks on the run-in side, especially in the axial direction ahead of the first thread flank, wherein the guide surface is offset vis-à-vis the (basic) (root) thread diameter of the thread in the radial direction.

The present description shall be presented with respect to a pedicle screw. The invention especially relates to a bone screw, however. Therefore the term pedicle screw is meant to be directed to a bone screw and vice versa.

A pedicle screw according to the invention includes a screw shank extending in the axial direction and including a male thread. On the screw head side the seating sleeve, the so called tulip, is connected to the screw shank. The tulip is substantially U-shaped having opposite wall portions, in general also referred to as sleeve flanks, and a gap (seat) for the rod or land formed therebetween and extending in the radial direction. The tulip is provided with a thread extending in the axial direction with which the clamping screw, also referred to as set screw, is screwed after inserting the rod into the tulip so as to clamp and fix the same.

According to the invention, the thread of the tulip may be, on the one hand, a female thread or, on the other hand, a male thread. In the first case the clamping screw preferably is in the form of a stud screw and in the second case is in the form of a threaded nut. The thread of the seating sleeve may be a single-pitch or multi-pitch thread. If the thread of the tulip is a female thread, the guide surface is offset vis-à-vis the outer diameter of the female thread outwardly in the radial direction or is extended in diameter. If the thread of the tulip is a male thread, the guide surface is offset vis-à-vis the inner diameter of the male thread inwardly in the radial direction or is reduced in diameter.

According to the invention, on the run-in side of the thread a run-in portion which is provided (with respect to the longitudinal axis of the thread) especially only on one side, is radially offset or modified in its diameter is provided for compensating deformations of the seating sleeve. This (one-sided) offset or this (one-sided) variation of diameter of the thread pitch serves for a guide for a clamping screw to be screwed into the thread. Due to this radial extension provided only at the thread run-in or ahead of the first thread flank (in a female thread) or radial reduction (in a male thread), the locking screw may radially yield somewhat from the axis and in this way immerse into the thread of the seating sleeve despite possible deformations of the seating sleeve. This guideway thus is configured so that the clamping screw can be easily positioned at the thread run-in even when the tulip is deformed. In this way, despite deformation a mutual engagement of the tulip thread and the clamp screw thread is ensured. In other words, between the clamping screw and the tulip a defined radial play is provided by which deformations of the tulip can be compensated. Due to this radial play, the clamping screw can be arranged easily and safely on the same and can be positioned relative to the tulip thread, even if the tulip is deformed. It is of particular advantage that the clamping screw can be correctly positioned on the pedicle screw by a surgeon even without sight and is guided and supported by a mutual thread engagement. Therefore no special effort or additional instruments are required to put the clamping screw into the position defined for screwing into the tulip with the required accuracy when it is attached to the tulip thread.

The seat of the clamping screw delimited by the guideway can also be detected haptically by the surgeon so that intended screwing is facilitated and misfits between the clamping screw and the pedicle screw are safely avoided. It is no longer required that a surgeon turns special attention to attaching the set screw, which entails considerable easement and time-saving. When the clamping screw guided along the guide surface is rotated about its own thread axis, the threads of the clamping screw and the tulip are made to engage. The clamping screw is advanced also in the axial direction due to its screwing motion. When the clamping screw is axially screwed in the direction of the pedicle screw, deformation of the latter, especially of the sleeve flanks can be reset. Upon screwing the clamping screw initially radially offset from the axis in the area of the thread run-in migrates back again radially with respect to the central thread axis. As a result, by the invention a clamping screw can be easily attached to a loaded and therefore deformed pedicle screw and can be screwed with the latter.

Advantageous embodiments of the invention will be discussed hereinafter in detail.

Preferably the guide surface is configured in a partly cylindrical, especially partly toroidal shape, about a central axis. The (pitch circle) diameter of the guide surface may be equal to the diameter of the thread of the tulip or may deviate therefrom. This central axis may be offset, as will be explained below, in the radial direction vis-à-vis the thread axis or may coincide with the latter.

The radial offset of the guide surface vis-à-vis the thread may be brought about by the central axis of the guide surface being offset vis-à-vis the thread axis of the tulip thread by an eccentricity. The diameter of the guide surface is preferably substantially equal to the diameter of the thread of the tulip. Preferably, the eccentricity is located on an imaginary straight line intersecting the thread axis and being orthogonal to the seat formed between the sleeve flanks for the rod, i.e. extending through the center of both the one and the other sleeve flank. It is an advantage of this embodiment that the guide surface is displaced toward the deformation, but otherwise exhibits substantially the diameter of the tulip thread. As a consequence, a radial play is brought about in the direction of the deformation so that even in the case of deformation of the tulip an easy and correct arrangement is possible while in other directions a clear guiding of the clamping screw is ensured.

Alternatively or additionally, the radial offset may be caused by the diameter of the guide surface being widened vis-à-vis the diameter of the tulip thread (if the tulip thread is a female thread) or by the diameter of the guide surface being reduced vis-à-vis the diameter of the tulip thread (if the tulip thread is a male thread). In this embodiment deformations can be perfectly compensated irrespective of their direction.

The direction as well as the size of the radial offset and, respectively, the eccentricity are dependent on the direction and the size of the deformation of the pedicle screw and are preferably adapted to the expected or occurring deformation, respectively. The radial offset and, resp., the eccentricity of the guide surface vis-à-vis the (outer) diameter of the tulip thread may range, according to the invention, from 0.05 mm to 0.5 mm, preferably from 0.05 mm to 0.3 mm, more preferred from 0.1 mm to 0.2 mm and especially preferred may be approximately 0.15 mm.

In one embodiment, in the case of a thread in the form of a female thread, the diameter of the guide surface is larger than the diameter of the thread. In the case of a thread in the form of a male thread, the diameter of the guide surface is smaller than the diameter of the thread. In one embodiment of the invention, the deviation of the diameter of the guide surface from the diameter of the thread is between approximately 1% and 20%, preferably between approx. 2% and 15%, especially preferred between approximately 5% and 10%.

In accordance with the invention, the guide surface may be formed in the axial direction on the run-in side outside the female thread and ahead of the first thread flank, respectively. This is of particular advantage because the clamping screw is to be rotated while being guided by means of the guide surface initially without engagement of the threads and without any significant axial load for engaging the threads until the two thread start-points are aligned with each other and are easily engaged. Alternatively or additionally it may be configured to extend in the axial direction into the tulip thread, especially into the first thread pitch, so that also a certain run-in portion or a certain depth of the tulip thread has a guiding effect on the clamping screw. In the latter case the bearing capacity of the thread is weakened, as is unavoidable by forming the guiding portion, only along a small part of the thread so that especially advantageously the bearing capacity of the thread remains almost unchanged.

In one embodiment of the invention the guide surface (enlarged or reduced in its diameter and configured coaxially with respect to the thread axis) may extend in the circumferential direction over the entire circumference of the sleeve flank. As an alternative, the guide surface (offset with its central axis with respect to the thread axis) can be restricted in the circumferential direction solely to a central portion of the sleeve flank.

In one embodiment the guide surface is configured in the axial direction to be in parallel to the thread axis of the tulip thread. In this way an especially stable guideway of the clamping screw is guaranteed. According to the invention, the axial depth and, resp., length of the guide surface aligned in parallel to the thread axis ranges from 0.3 mm to 4 mm, preferably from 0.5 mm to 2.5 mm and especially preferred amounts to approx. 0.6 mm.

Alternatively or additionally, the guide surface is inclined partly or completely with respect to the thread axis by an angle α. Then it may have a guide surface portion parallel to the tulip thread axis and an inclined guide surface portion or may be completely inclined. The angle α may be inclined between 1° and 60°, preferably between 3° and 40°, more preferred between about 5° and 20° and especially preferred between 7° and 10°. The depth of the guide surface inclined by the angle α vis-à-vis the thread axis and, resp., of the guide surface portion may range, according to the invention, from 0.3 mm to 4 mm, preferably from 0.5 mm to 2.5 mm and especially preferred may be approximately 0.6 mm. In this embodiment it is especially easy to introduce the clamping screw into the guideway.

The guide surface may be formed by a machining process, e.g. by milling.

The tulip thread may be a counterdraft thread, especially a counterdraft buttress thread. The thread pitch or pitches may include a T-shaped or L-shaped cross-section. In this way especially clamping or self-locking of the clamping screw within the thread can be brought about.

In one embodiment the guide surface of both sleeve flanks (having the same axial length) is formed only on the sleeve flank whose first thread flank is arranged at a greater axial depth. This may facilitate attaching the clamping screw without having to vary the first thread flank formed on the opposite sleeve flank and, resp., the first thread pitch and having to act on the thread per se, respectively.

According to the invention, the seating sleeve may be adapted to be positioned as a separate element, especially angularly positioned, on the bone screw. It may also be said that the screw system according to the invention may be a mono-axial or a poly-axial system. This means that the seating sleeve may be formed integrally with the bone screw or that the seating sleeve may be adapted to be positioned as a separate element, especially may be arranged to be angularly positioned with respect to the bone screw on the latter. In the case of a mono-axial bone screw the seating sleeve is tightly connected to the shank thereof, for example integrally formed, welded or soldered. In the case of a poly-axial bone screw, such screw may include a male thread portion manufactured as separate shank component having a spherical or (semi)spherical screw head. On the latter the seating sleeve may be arranged to be angularly positioned. The seating sleeve may grip behind the screw head in the transitional area toward the bone screw shank. In this manner, the seating sleeve can be swiveled and/or rotated relative to the shank after screwing the bone screw into a bone so as to obtain a desired position and alignment substantially independently of the alignment of the shank. The counterdraft prevents the seating sleeve from being removed from the shank head. Subsequently, the seating sleeve may be fixed in position on the screw head of the bone screw by means of the clamping screw with an interposed rod/land or by means of an additional screw element.

BRIEF DESCRIPTION OF THE DRAWING FIGURES

Further features and advantages of the present invention will result from the following exemplary and non-limiting description of the invention by way of a pedicle screw system as an example of a bone screw system by way of Figures. These Figures are merely schematic and only aid to understand the invention. They illustrate in.

DETAILED DESCRIPTION

FIGS. 1 through 4 illustrate a pedicle screw system 1 according to the invention. It includes a pedicle screw 2, a seating sleeve 3, also referred to as tulip 3, as well as a clamping screw 4. The seating sleeve 3 may be formed basically integrally with the pedicle screw 2 or as a separate component. The latter may be arranged movably on the pedicle screw 2 so that a poly-axial pedicle screw system is formed in which the seating sleeve 3 is adapted to be angularly positioned relative to the pedicle screw 2. The following description relates to a poly-axial pedicle screw system, but it is also applicable to a seating sleeve 3 that is formed integrally with the pedicle screw 2.

On the side opposite to the seating sleeve 3 the pedicle screw 2 is provided with a male thread 5 by which it may be screwed into a pedicle canal of a vertebra (by way of example of a bone). For this purpose, on the side of the seating sleeve 3 the pedicle screw 2 is provided with an engagement for wrenches and screwdrivers 6. The seating sleeve 3 has a substantially U-shaped configuration including a hole 8 introduced to the same in the axial direction and including a female thread 7. In other words, the seating sleeve 3 may be formed by removing material from a hollow cylinder on radially opposed sides in the axial direction and by providing the hole of the hollow cylinder with the female thread 7. Two radially opposed sleeve wall portions 9, 10 whose inner surfaces facing each other delimit the hole 8 and are provided with the female thread 7 are left from the hollow cylinder.

Figure 1:
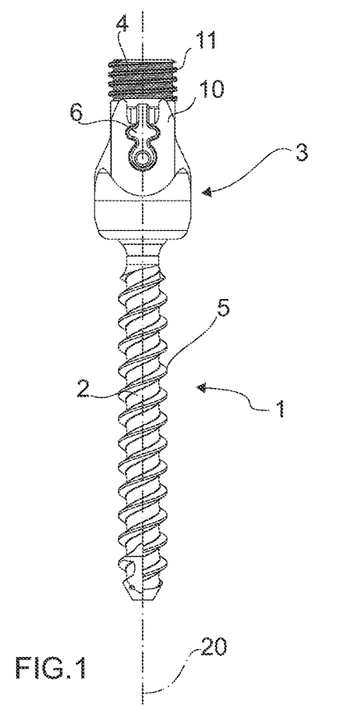
FIG. 1 a pedicle screw according to the invention in a front view.
Figure 2:
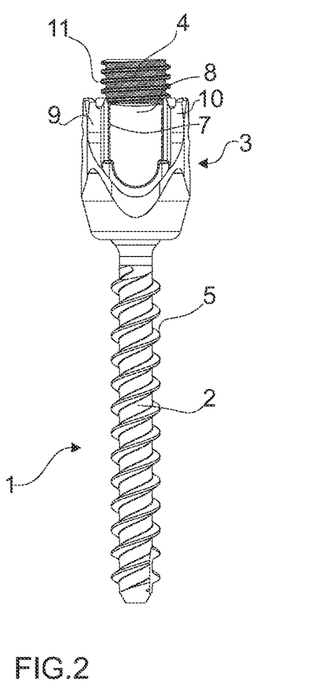
FIG. 2 the pedicle screw of FIG. 1 in a side view.
Figure 3:
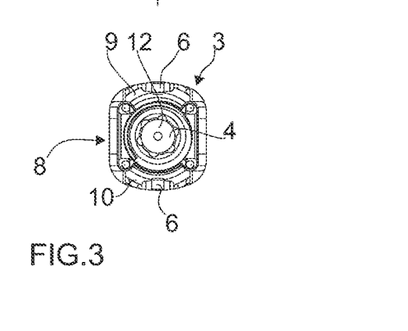
FIG. 3 the pedicle screw of FIG. 1 in a top view.
Figure 4:
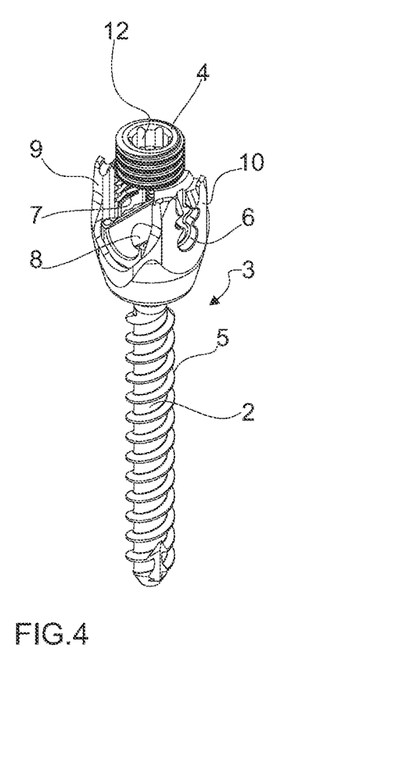
FIG. 4 the pedicle screw of FIG. 1 in a perspective view.

The clamping screw 4 in the form of a stud screw common for this purpose is provided with a male thread 11 and a front-side tool holder 12 shown in FIG. 3, for example a hexagon socket.

Figure 5:
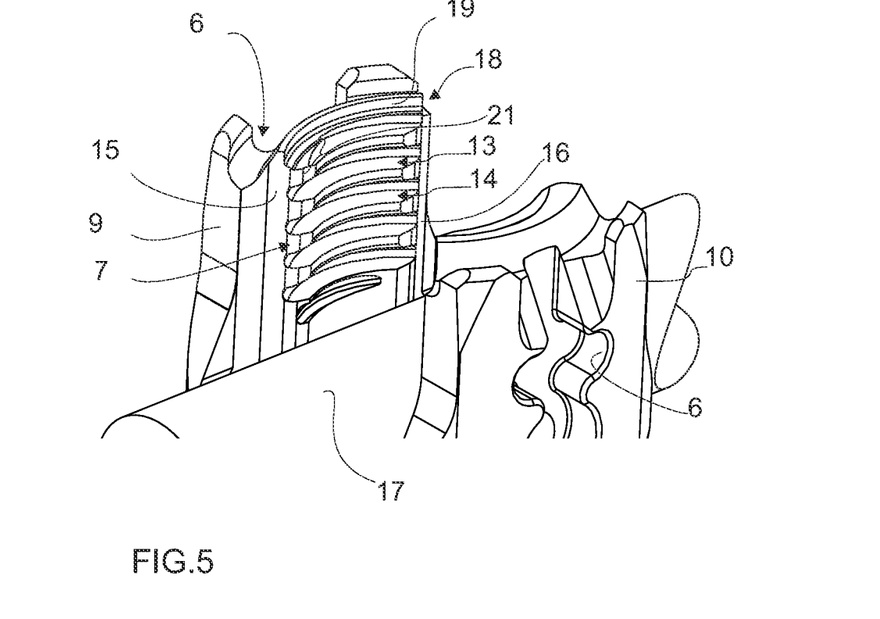
FIG. 5 part of the tulip of a pedicle screw of a first embodiment of the invention in a perspective view, FIG. 6 the detail of FIG. 5 in a perspective representation from a different viewing direction, FIG. 7 a perspective view of part of the tulip of the first embodiment with a clamping screw being attached to the guide surface, FIG. 8 the tulip of the first embodiment of the FIGS. 5 to 7 in a side view with a magnified detail and FIG. 9 the tulip of a second embodiment in a side view with a magnified detail.

FIG. 5 illustrates the female thread 7 of a first embodiment of the invention in a perspective view. The female thread 7 is a single-start thread. It includes one single thread pitch having a first thread portion 13 in the first sleeve wall portion 9, a second thread pitch portion not evident from the Figures in the opposite sleeve wall portion 10, a third thread pitch portion 14 in the first sleeve wall portion 9, a fourth thread pitch portion not evident from the Figures in turn in the opposite sleeve wall portion 10 etc. The thread pitch portions 13, 14 in the first sleeve wall portion 9 include a run-in side 15 and a run-out side 16. The thread pitch portions in the second sleeve wall portion 10 equally include a run-in side and a run-out side. In the seat 8 a rod 17 is inserted which is clamped in the seat 8 by means of the clamping screw 4 screwed into the tulip 3 (not shown in FIG. 5).

Figure 6:
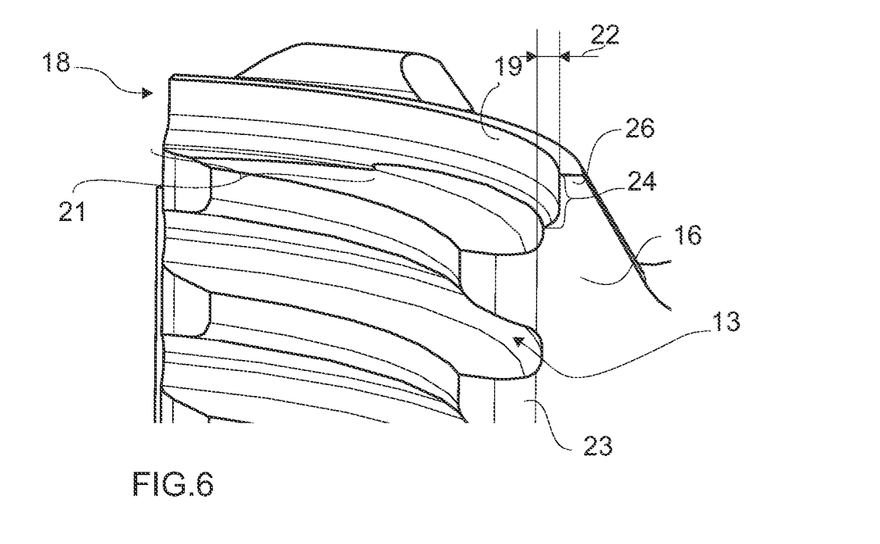
Figure 7:
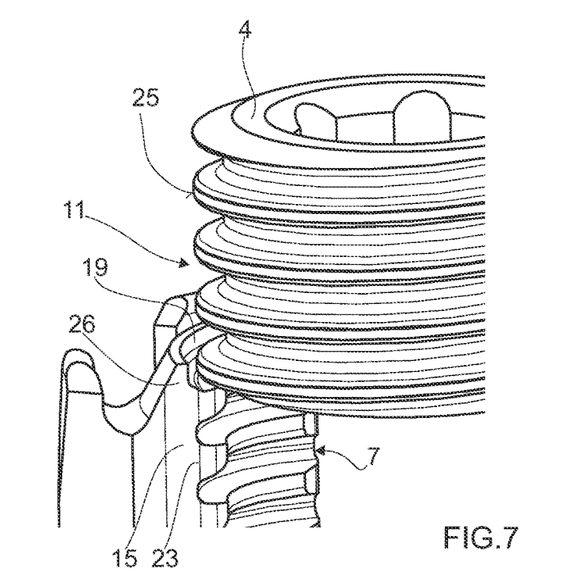

FIGS. 5, 6 and 7 illustrate a guideway 18 formed at the tulip 3 on the thread run-in side, i.e. on the side of the tulip facing away from the pedicle screw 2, and having a guide surface 19 extending substantially in the circumferential direction. In the first embodiment shown in FIGS. 5, 6 and 7 the guide surface 19 largely extends in the axial direction, i.e. substantially in parallel to the thread axis 20. The guideway 18 does not only extend on the run-in side ahead of the thread run-in but also into the tulip thread 7 with a portion 21 marked in FIGS. 5 and 6. The radial offset or the eccentricity 22 of the guide surface 19 compared to the thread 7, in this case the outer diameter 23 of the thread 7, is marked in FIG. 6. As the tulip thread 7 is a female thread, the diameter of the guide surface 19 is widened in the radial direction as compared to the outer diameter 23 of the tulip thread 7. In other words, in the area of the guide surface 19 the "thread depth" ahead of the axially first thread flank is larger than the (normal) thread depth between the axially successive thread flanks. For example, the guide surface 19 is formed by means of a machining method. The one sleeve flank 9 of the seating sleeve 3 may be machined, for example, in the area of the thread run-in 26 or ahead of the first thread flank by means of a miller or any other suitable tool so as to manufacture the guide surface 19.

It is especially evident from FIG. 7 that the guide surface 19 is formed merely on the sleeve flank 9 whose axially first thread flank is arranged more deeply (by half a thread pitch) than in the opposite sleeve flank 10 and thus offers space for the guide surface 19 without having to modify the thread geometry or the thread length on the opposite sleeve flank 10.

In the case of deformation of the tulip 3, especially when a sleeve wall 9, 10 is bent in the direction of the thread axis 20, the clamping screw 4 may be introduced into the guideway 18 in the axial direction, namely by the degree of the depth 24 of the guideway 18. Accordingly, the outer edge 25 of the male thread 11 of the clamping crew 4 abuts against the guide surface 19, but only as long as the male thread 11 of the clamping screw 4 has not yet engaged in the tulip thread 7. Being guided through the guideway 18 in this manner the clamping screw 4 can be positioned above the tulip thread 7 by a surgeon even without having an unobstructed view onto the pedicle screw 2 and in the case of deformation of the tulip 3. In the case of continuous guiding the clamping screw 4 then may be rotated about its central axis with respect to the tulip 3 for engaging its male thread 11 in the tulip thread 7. As soon as the two threads are engaged, the clamping screw 4 is advanced in the axial direction by this engagement and penetrates the female thread 7, thus causing the deformation of the tulip 3 to be reversed substantially completely and the initially radially escaped clamping screw to coaxially realign with respect to the thread axis 20 of the tulip thread 7. This state of screwing in the clamping screw 4 is shown in FIG. 7 where it is evident that upon engagement of the two threads 7, 11 the outer side 25 of the clamping screw 4 does no longer contact the guide surface 19, but contacts the outer diameter 23 of the thread 7.

Figure 8:
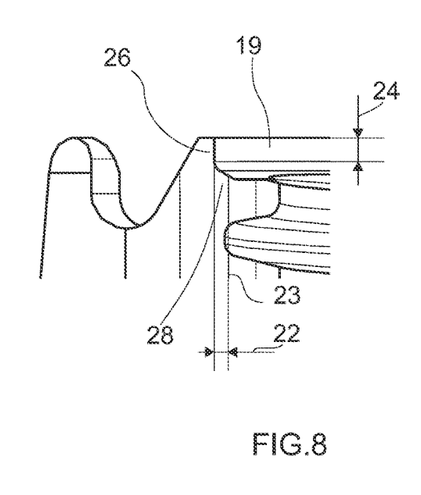
Figure 9:
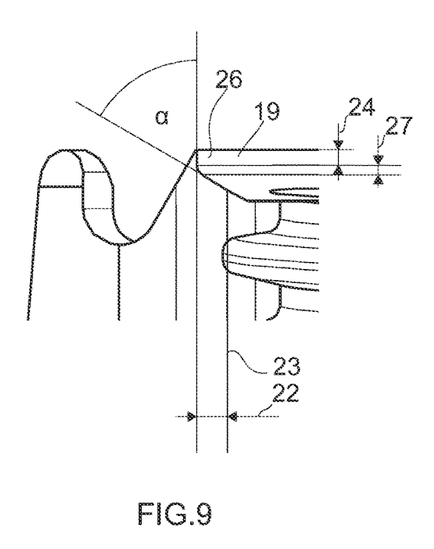

FIGS. 8 and 9 compare the first embodiment of the invention (FIG. 8) to a second embodiment of the invention (FIG. 9), with a cutout illustrating the guideway 18 being shown in a clearly magnified manner. As already explained in the foregoing with respect to FIGS. 5 and 6, the guide surface 19 in the first embodiment extends in the axial direction substantially completely in parallel to the thread axis 20. It is offset against the outer diameter 23 of the tulip thread 7 in the radial direction, i.e. orthogonally to the thread axis 20, by the offset 22 or, resp., the eccentricity 22. In the first embodiment shown in FIG. 8 the guide surface 19 has a depth 24 and runs out into the thread 7 with a rounded run-out 28. In the second embodiment shown in FIG. 9 the guide surface 19 is divided into a first guide surface portion 29 and a second guide surface portion 30. The first guide surface portion 29 extends in the axial direction substantially completely in parallel to the thread axis 20 and has a depth 24. The second guide surface portion 30 is inclined vis-à-vis the thread axis 20 by an angle α and exhibits a run-out depth 27. This embodiment allows for smoother reforming of a given deformation of the sleeve flank 9 when the clamping screw 4 is screwed into the tulip thread 7.

The invention claimed is:

1. A bone screw comprising:
   a screw head;
   a seating sleeve or tulip provided on the screw head and having two sleeve flanks provided with a thread between which sleeve flanks a slit-shaped seat for a rod is formed for surgical connection of adjacent bone screws; and
   a guide surface formed on a run-in side on at least one of the sleeve flanks, the guide surface extending in a circumferential direction for a clamping screw adapted to be screwed into the thread, the guide surface either being offset vis-à-vis a thread diameter of the thread in a radial direction or the guide surface having a varied diameter, wherein the guide surface is partially defined within the thread,
   wherein a depth of the guide surface meets at least one of the following: (a) the depth of the guide surface aligned in parallel to a thread axis ranges from about 0.3 mm to about 4 mm, and (b) the depth of the guide surface and a guide surface portion inclined with respect to the thread axis by an angle α ranges from about 0.3 mm to about 4 mm.

2. The bone screw according to claim 1, wherein the guide surface is formed on only one sleeve flank, said one sleeve flank including a first thread pitch of the thread.

3. The bone screw according to claim 1, wherein the guide surface is formed in a partly cylindrical shape about a central axis offset against a thread axis of the thread about an eccentricity.

4. The bone screw according to claim 1, wherein the thread is a female thread, and the diameter of the guide surface is larger than the diameter of the thread.

5. The bone screw according to claim 1, wherein the guide surface meets at least one of the following: (a) the guide surface is formed in an axial direction on the run-in side outside of the thread and (b) the guide surface extends in the axial direction into the thread.

6. The bone screw according to claim 1, wherein the guide surface meets at least one of the following: (a) the guide surface extends in the circumferential direction over an entire periphery of the sleeve flank, and (b) the guide surface extends in an axial direction from an axial end of the sleeve flank up to a first thread flank axially provided on the sleeve flank.

7. The bone screw according to claim 1, wherein the guide surface meets at least one of the following: (a) the guide surface is formed in an axial direction in parallel to a thread axis of the female thread and (b) the guide surface is inclined partly or completely with respect to the thread axis by an angle α between about 1° and about 60°.

8. The bone screw according to claim 1, wherein the seating sleeve is arranged to be positioned as a separate element on the bone screw.

9. The bone screw according to claim 1, wherein the thread is a male thread, and the diameter of the guide surface is smaller than the diameter of the thread.

10. The bone screw according to claim 1, wherein the guide surface comprises a first guide surface portion extending parallel to a thread axis of the thread.

11. The bone screw according to claim 10, wherein the first guide surface portion is entirely offset vis-à-vis the thread diameter in the radial direction.

12. The bone screw according to claim 10, wherein the guide surface comprises a second guide surface portion running into the thread with a rounded run-out.

13. The bone screw according to claim 10, wherein the guide surface comprises a second guide surface portion being inclined vis-à-vis the thread axis by a predetermined angle and exhibiting a run-out depth.

14. The bone screw according to claim 10, wherein the guide surface consists of the first guide surface portion and a second guide surface portion, the first guide surface portion having a predetermined depth and being entirely offset vis-à-vis the thread diameter in the radial direction, the second guide surface portion either running into the thread with a rounded run-out or being inclined vis-à-vis the thread axis by a predetermined angle and exhibiting a run-out depth.

15. A bone screw comprising:
a screw head;
a seating sleeve or tulip provided on the screw head and having two sleeve flanks provided with a thread between which sleeve flanks a slit-shaped seat for a rod is formed for surgical connection of adjacent bone screws; and
a guide surface formed on a run-in side on at least one of the sleeve flanks, the guide surface extending in a circumferential direction for a clamping screw adapted to be screwed into the thread, the guide surface either being offset vis-à-vis a thread diameter of the thread in a radial direction or the guide surface having a varied diameter, wherein
the guide surface comprises a first guide surface portion extending parallel to a thread axis of the thread and
wherein the guide surface comprises a second guide surface portion running into the thread with a rounded run-out.

16. The bone screw according to claim 15, wherein the first guide surface portion is entirely offset vis-à-vis the thread diameter in the radial direction.

17. The bone screw according to claim 15, wherein the guide surface comprises a second guide surface portion being inclined vis-à-vis the thread axis by a predetermined angle and exhibiting a run-out depth.

18. A bone screw comprising:
a screw head;
a seating sleeve or tulip provided on the screw head and having two sleeve flanks provided with a thread between which sleeve flanks a slit-shaped seat for a rod is formed for surgical connection of adjacent bone screws; and
a guide surface formed on a run-in side on at least one of the sleeve flanks, the guide surface extending in a circumferential direction for a clamping screw adapted to be screwed into the thread, the guide surface either being offset vis-à-vis a thread diameter of the thread in a radial direction or the guide surface having a varied diameter,
wherein the guide surface comprises a first guide surface portion extending parallel to a thread axis of the thread, and
wherein the guide surface consists of the first guide surface portion and a second guide surface portion, the first guide surface portion having a predetermined depth and being entirely offset vis-à-vis the thread diameter in the radial direction, the second guide surface portion either running into the thread with a rounded run-out or being inclined vis-à-vis the thread axis by a predetermined angle and exhibiting a run-out depth.

* * * * *